(12) United States Patent
Schöb

(10) Patent No.: US 6,711,943 B1
(45) Date of Patent: *Mar. 30, 2004

(54) METHOD FOR THE DETERMINATION OF THE VISCOSITY OF A LIQUID SUCH AS BLOOD

(75) Inventor: Reto Schöb, Volketswil (CH)

(73) Assignee: Levitronix LLC, Waltham, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/333,780

(22) Filed: Jun. 15, 1999

(30) Foreign Application Priority Data

Jun. 22, 1998 (EP) .............................. 98810568

(51) Int. Cl.⁷ ........................ G01N 11/14; G01N 11/10
(52) U.S. Cl. ..................................... 73/54.28; 73/54.38
(58) Field of Search .......................... 73/54.01, 54.28, 73/54.29, 54.31, 54.33, 54.38

(56) References Cited

U.S. PATENT DOCUMENTS

| | | | |
|---|---|---|---|
| 4,485,450 A | * 11/1984 | Characklis et al. ........ 73/54.31 |
| 4,534,210 A | * 8/1985 | Reeves ..................... 73/54.31 |
| 4,781,525 A | 11/1988 | Hubbard | |
| 5,725,357 A | 3/1998 | Nakazeki | |
| 5,798,454 A | * 8/1998 | Nakazeki et al. .......... 73/54.28 |

FOREIGN PATENT DOCUMENTS

| | | |
|---|---|---|
| CH | 683322 A5 | 2/1994 |
| DE | 19634180 A1 | 2/1997 |
| WO | WO97/24596 | 7/1997 |

* cited by examiner

Primary Examiner—Michael Cygan
(74) Attorney, Agent, or Firm—Townsend and Townsend and Crew, LLP

(57) ABSTRACT

In a method for the determination of the viscosity ($\eta$) of a liquid, e.g. of blood, which is forwarded by a pump, e.g. a blood pump, said pump having a rotor for the forwarding of the liquid from the inlet of the pump to the outlet, the rotor is used for the determination of the viscosity ($\eta$). For the determination of the viscosity ($\eta$) of the liquid no spatial deflection of the rotor from its operating position takes place, but rather the rotor is left in its operating position and the viscosity ($\eta$) is determined from measurement parameters of the pump or of the rotor respectively.

10 Claims, 2 Drawing Sheets

METHOD FOR THE DETERMINATION OF THE VISCOSITY OF A LIQUID SUCH AS BLOOD

BACKGROUND OF THE INVENTION

1. Field of the Invention

The invention relates to a method for the determination of the viscosity of a liquid, e.g. of blood, which is forwarded by a pump, e.g. a blood pump.

2. Description of the Prior Art

Pumps, in particular blood pumps, which are used for example in heart-lung machines (as a substitute for the pumping function of the heart) have an inlet and an outlet for the liquid to be forwarded, thus here the blood. Furthermore, pumps of this kind have a rotor which forwards the liquid to be forwarded, thus here the blood, from the inlet to the outlet. Especially in blood pumps, which are used in heart-lung machines, one of the parameters which must be continuously monitored is the viscosity of the blood. But the monitoring of the viscosity can also be required or desirable respectively in pumps other than blood pumps.

A blood pump in which it is possible to determine the viscosity of the blood is for example known from U.S. Pat. No. 5,725,357. In the pump described there the rotor is actively magnetically journalled in the axial direction. A part of the magnetic bearing is admittedly formed with the help of permanent magnets; the other part of the magnetic bearing is however formed with the help of regulatable electromagnets in order to be able to actively regulate the bearing, which is formed of two parts.

The viscosity determination is carried out in accordance with DE-A-196 13 388 in such a manner that a disturbance signal with a definite amplitude and a definite frequency is supplied to the regulation circuit for the magnetic bearing, e.g. with a frequency of 70 Hz. The rotor, which is located in a certain position without the disturbance signal, is axially deflected out of this position by the disturbance signal. If now the viscosity of the blood changes, the axial deflection of the rotor also changes particularly noticeably at the named disturbance frequency of 70 Hz. If then the dependence of the axial deflection of the rotor on the respective speed of rotation of the rotor at a frequency of the disturbance signal of 70 Hz is also taken into account, then the viscosity of the blood can be determined via the respective axial deflection of the rotor.

This blood pump or the described procedure respectively is disadvantageous in so far as an actively regulatable axial journalling of the pump rotor must be provided in order to be able to impress the disturbance signal via the active journalling. On the other hand it is not possible to determine the viscosity in the above described manner with pumps in which the axial journalling of the rotor is mechanical because the mechanical journalling of the rotor is rigid in the axial direction so that a deflection of the rotor in the axial direction can not take place. A determination of the viscosity of the blood is also not possible in this manner in passive axial magnetic bearings, in which the rotor is journalled in the axial direction through reluctance forces, because an active excitation of the journalling in passive bearings—the property "passive" says precisely this—is simply not possible. Thus the described procedure is suitable only for pumps with an active axial magnetic journalling of the rotor; for pumps with rotors which are mechanically journalled in the axial direction and also for pumps with a passive axial magnetic journalling the described procedure is not suitable.

SUMMARY OF THE INVENTION

An object of the invention is therefore to propose a method by means of which it is possible to determine the viscosity of the forwarded liquid, e.g. blood, in a pump, e.g. a blood pump, with as little cost and complexity as possible, with the type of the journalling of the rotor, in particular the type of the axial journalling, should be freely selectable. In particular the method should naturally be suitable for magnetic journallings of the rotor which are typically used in blood pumps.

For the determination of the viscosity of a liquid, e.g. blood, which is forwarded by a pump, e.g. a blood pump, said pump having a rotor for the forwarding of the liquid from the inlet of the pump to the outlet, the rotor is likewise utilised for the determination of the viscosity. However no active excitation of the rotor for the axial deflection out of its operating position takes place for the determination of the viscosity of the liquid, but rather the rotor is left in its operating position and the viscosity is determined from the measurement parameters of the pump or of the rotor respectively. Thus the type of the journalling of the rotor, in particular the type of the axial journalling of the rotor, is freely selectable. Naturally the method is especially suitable also for magnetic journallings of the rotor, such as are typically used in blood pumps, in particular also for passive axial magnetic journallings of the rotor.

As measurement parameters the drive torque or the drive current respectively of the rotor and/or the speed of rotation of the rotor can be measured. These are parameters which can be easily measured outside the pump. This holds both for the drive torque of the rotor (or, more precisely: of the motor which drives the rotor), since the drive torque is approximately directly proportional to the drive current and a determination can be made via a known functional relationship for absolute exactness, and for the speed of rotation, which is approximately proportional to the voltage at the rotor (and a determination can be made via a known functional relationship for absolute exactness), so that for practical purposes the voltage at the rotor (or, more precisely: at the motor which drives the rotor) can be measured as a measure for the speed of rotation. In speed-of-rotation regulated motors, which are motors which are regulated to a constant speed of rotation, it is sufficient in principle to measure only the drive torque (the speed of rotation is approximately constant). In torque regulated motors, which are motors which are regulated to a constant drive torque or to a constant drive current respectively, it is sufficient in principle to measure only the speed of rotation (the drive torque or the drive current respectively is approximately constant). Naturally it is always possible and naturally the exact procedure to measure both the speed of rotation as well as the drive torque or the drive current respectively. From the values for the drive torque or the drive current respectively and/or the speed of rotation of the rotor the viscosity of the liquid is then determined.

In this a plurality of measurements of the drive torque or the drive current respectively and/or the speed of rotation of the rotor can be carried out for the determination of the viscosity so that a plurality of (individual) values for the viscosity are determined. From this plurality of values for the viscosity, an average viscosity is then determined which then represents the value for the viscosity. Through this the precision of the value for the viscosity can be increased. Further method variants differ in that they are carried out either with the outlet of the pump closed or with the outlet of the pump open, thus quasi "on line".

In a first series of advantageous method variants the pump outlet is closed prior to the determination of the viscosity with the help of the measurement parameters. During a heart operation the outlet must be clamped off anyway for reasons of the operation so that the time in which the outlet is closed can be used for the determination of the viscosity.

In this the measurements of the drive torque or the drive current respectively and/or the speed of rotation of the rotor can be effected through a trigger signal which, after the closure of the pump outlet, is transmitted further to a control system which then initiates the measurements of the drive torque or the drive current respectively and/or the speed of rotation of the rotor.

A trigger signal of this kind can for example be produced by a closure apparatus for the closing of the pump outlet, e.g. a valve, and conducted to the control system as soon as the pump outlet is closed.

Another possibility consists in that the trigger signal is produced by a through-flow measurement apparatus which is arranged at the pump outlet and is conducted to the control system as soon as no more through-flow is determined at the pump outlet. If no more through-flow is determined at the pump outlet, this means that the pump outlet is closed and the measurements of the drive torque or the drive current respectively and/or the speed of rotation of the rotor for the determination of the viscosity can be initiated.

Yet another possibility consists in that the trigger signal is produced by a pressure measurement apparatus which is arranged at the pump outlet and is conducted to the control system as soon as a pressure is determined at the pump outlet which exceeds a threshold value at a given speed of rotation of the rotor. The exceeding of this threshold pressure also means that the pump outlet is closed and that the measurements of the drive torque or the drive current respectively and/or the speed of rotation of the rotor for the determination of the viscosity can be initiated.

Furthermore, in a pump with regulation of the speed of rotation an abrupt drop in the drive torque arising after the closing of the pump outlet can be detected and the trigger signal thereupon conducted to the control system. In a pump with regulation of the speed of rotation namely the drive torque or the drive current respectively drops abruptly after the closure of the pump outlet because no more blood can be forwarded and the blood which is located in the pump very rapidly has the same speed as the pump rotor so that only a low drive torque or a low drive current respectively is still required for maintaining this speed.

Conversely, in a pump with drive torque regulation or drive current regulation respectively an abrupt rise in the speed of rotation which takes place after the closure of the pump outlet can be detected and the trigger signal thereupon conducted to the control system. In a pump with drive torque regulation or drive current regulation respectively namely the speed of rotation rises very rapidly after the closure of the pump outlet because no more blood can be forwarded and the blood which is located in the pump very rapidly has the same speed of rotation as the rotor so that only a low drive torque or a low drive current is still required to maintain this speed. Nevertheless the same drive torque or the same drive current respectively is still available as when the pump outlet is open, which has an acceleration of the rotor (speed of rotation increase) and of the liquid as a result.

In a second series of advantageous method variants the measurements of the drive torque or drive current respectively and/or speed of rotation of the rotor are carried out with the pump inlet open and the pump outlet open, thus quasi "on line" during the operation. This method variant can be carried out at any desired time (e.g. at any desired time during a heart operation) except at just those times at which the pump outlet is closed.

In this method variant the determination of the viscosity can take place in such a manner that the speed of rotation of the rotor is modulated about a nominal speed of rotation with a modulation amplitude and a modulation frequency, with practically no or only a slight change of the through-flow being produced at the outlet of the pump by the modulation. As a result of the inertia of the liquid, substantially no change in the through-flow takes place; however, a fluctuation in the drive torque or in the drive current respectively is produced by the modulation. The viscosity is then determined from the modulation amplitude of the speed of rotation and from the amplitude of the fluctuation of the drive torque or the drive current respectively resulting therefrom.

The determination of the viscosity can also take place in such a manner that the drive torque or the drive current respectively is modulated about a nominal drive torque or a nominal drive current respectively with a modulation amplitude and a modulation frequency, with practically no or only a slight change of the through-flow being produced at the outlet of the pump by the modulation, with however a fluctuation in the speed of rotation being produced.

Here as well substantially no change in the through-flow takes place as a result of the inertia of the liquid. The viscosity is then determined from the modulation amplitude of the drive torque or of the drive current respectively and the amplitude of the fluctuation of the speed of rotation resulting therefrom.

Since all of the above described method variants are especially also suitable for blood pumps, a pump with a magnetic journalling of the rotor is advantageously used, such is typically the case in blood pumps (for a number of reasons, e.g. contamination).

DETAILED DESCRIPTION OF THE PREFERRED EXEMPLARY EMBODIMENTS

Figure 1:
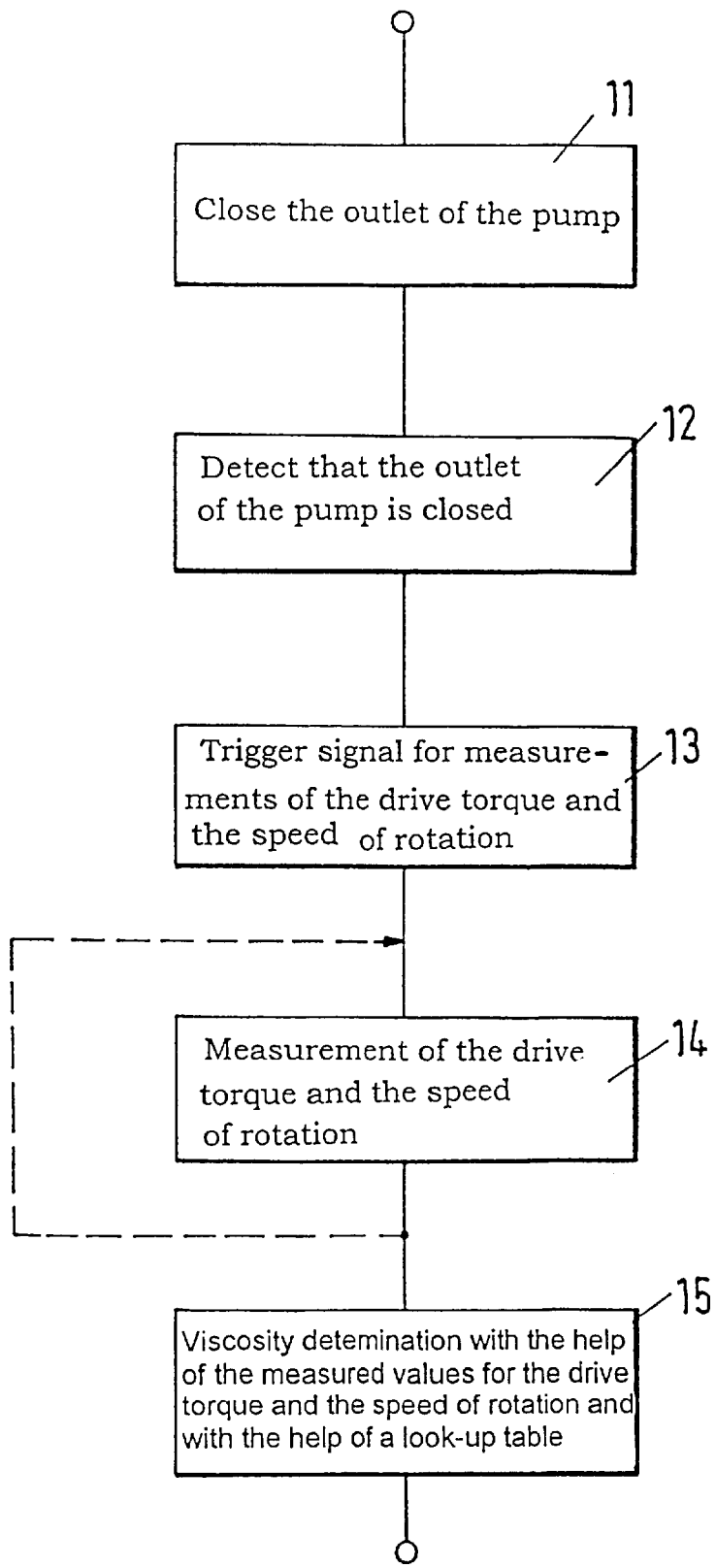
FIG. 1 illustrates a first embodiment variant of the method in accordance with the invention for the determination of the viscosity in the form of a flow diagram (with the outlet of the pump closed)

In FIG. 1 a flow diagram of a method variant of the method in accordance with the invention for the determination of the viscosity is illustrated. A first series of method variants could proceed in accordance with this flow diagram in which the determination of the viscosity takes place with the pump outlet closed.

For this it should be stated in advance that the following simplified relation holds for the moment of friction of liquids in pumps:

$$M_R \sim K_G \cdot \eta \cdot \omega \qquad (I)$$

in which the individual variables signify the following:

$M_R$ the moment of friction of a liquid, $K_G$ a geometric factor,

η the dynamic viscosity of the liquid,
ω the angular frequency of the pump rotor.

When the pump outlet is closed the through-flow through the pump becomes zero, which means in other words that the total drive power is converted into liquid friction, thus that the drive torque corresponds to the moment of friction.

$$M_A = M_R$$

with $M_A$ drive torque $M_R$ moment of friction, or as a result of relation (I) it follows that the viscosity is proportional to the drive torque:

$$\eta \sim M_A$$

In practice the relationships in a pump are somewhat more complicated (as a result of turbulent flow etc.); nevertheless there is a unique functional relationship between the viscosity, the speed of rotation of the rotor (or the angular frequency respectively) and the drive torque:

$$107 = f(M_A, \omega, \qquad \text{(II)}$$

This functional relationship can be determined by means of measurements for each pump and can for example be stored in the memory of a microprocessor e.g. in the form of a look-up table. In this variant embodiment of the method in accordance with the invention a look-up table of this kind has already been determined for the respective pump prior to the operation of the pump and stored in the memory of the microprocessor.

In accordance with FIG. 1 this exemplary embodiment of the method for the determination of the viscosity proceeds in such a manner that the outlet of the pump is closed by means of a closure apparatus in a first step 11. During a heart operation the outlet of a pump of this kind, which is used e.g. in a heart-lung machine, is clamped off anyway for reasons of the operation so that the time in which the outlet is closed can be used for the determination of the viscosity.

Once the outlet is closed, the measurement of the drive torque or the drive current respectively and/or the speed of rotation of the rotor can be initiated with the help of a trigger signal which is conducted to a control system. In a pump with regulation of the speed of rotation (that is, with a regulation to a constant speed of rotation) it is sufficient in principle when the drive torque or the drive current respectively is measured (the speed of rotation is of course approximately constant); in a pump with a regulation of the drive torque or of the drive current respectively (that is, with a regulation to a constant drive torque or a constant drive current respectively) it is sufficient in principle to measure the speed of rotation (the drive torque or the drive current respectively is of course approximately constant). Naturally it is possible and also exact to measure both the drive torque or the drive current respectively as well as the speed of rotation. In order that a trigger signal can be produced for the initiation of a measurement process, it must first be detected in a step 12 that the outlet of the pump is closed. A trigger signal of this kind can for example be produced by the closure apparatus itself, e.g. an (electrically actuatable) valve of the heart-lung machine, and conducted to the control system as soon as the pump outlet is closed.

Another possibility consists in providing a through-flow measurement apparatus at the pump outlet which produces the trigger signal and conducts it to the control system as soon as no more through-flow is determined at the pump outlet. This means namely that the pump outlet is closed.

Again another possibility consists in providing a pressure measurement apparatus at the pump outlet which produces the trigger signal and conducts it to the control system as soon as a pressure is determined at the pump outlet which exceeds a threshold value at a given speed of rotation of the rotor. The exceeding of this threshold pressure means that the pump outlet is closed.

Furthermore, the closed outlet in a pump with regulation of the speed of rotation (that is, in a pump which is regulated to a constant speed of rotation) can be detected through an abrupt drop of the drive torque which arises after the closure of the pump outlet and the trigger signal can thereupon be conducted to the control system. In a pump with regulation of the speed of rotation, namely, the drive torque or the drive current of the rotor respectively drops abruptly after the closure of the pump outlet because no more blood can be forwarded and the blood which is located in the pump very rapidly has the same rotational speed as the pump rotor, so that only a low drive torque or a low drive current respectively is still required for maintaining this rotational speed.

Conversely, the closed outlet in a pump with drive torque regulation or drive current regulation respectively (that is, in a pump which is regulated to a constant drive torque or to a constant drive current respectively) can be detected through an increase of the speed of rotation which arises abruptly after the closure of the pump outlet and the trigger signal can thereupon conducted to the control system. In a pump with drive torque regulation or drive current regulation respectively, namely, the speed of rotation increases very rapidly after the closing of the pump outlet because no more blood can be forwarded and the blood which is located in the pump very rapidly has the same speed of rotation as the rotor so that only a low drive torque or a low drive current respectively is still required for maintaining this speed. Nevertheless, the same drive torque or the same drive current respectively is still available as when the pump outlet is open, which has an acceleration of the rotor (speed of rotation increase) and of the liquid as a result.

After the closed outlet of the pump has been detected in step 12 and the trigger signal for the measurements of the drive torque and the speed of rotation of the rotor has been released in step 13, the measurement of the drive torque and/or speed of rotation is initiated by the control system.

The measurement of the drive torque and/or the speed of rotation of the rotor is done in a step 14. In this the drive torque can be measured in such a manner that the drive current of the motor which drives the pump is measured. The drive current is approximately directly proportional to the drive torque (see above), for which reason the drive current is a direct measure for the drive torque in practice and the drive torque can easily be calculated from the measured value for the drive current. The speed of rotation of the rotor can either be directly measured by means of a speed of rotation measurement device, which is known per se, or the drive voltage of the motor which drives the pump can be measured. The drive voltage is approximately directly proportional to the speed of rotation of the rotor (see above), for which reason the drive voltage is a direct measure for the speed of rotation of the rotor and the speed of rotation of the rotor can easily be calculated from the drive voltage. The values for the drive torque and the speed of rotation of the rotor are thus available after carrying out the measurements in step 14.

In a step 15 the viscosity which results from the measured values for the drive current and the speed of rotation is now looked up in the look-up table with the help of the microprocessor. If in this the values measured in step 14 for the drive current and the speed of rotation of the rotor are not present exactly in the look-up table in the memory of the microprocessor, then the usual interpolation methods are used.

A plurality of measurements of the drive torque or the drive current respectively and/or the speed of rotation of the rotor can also be carried out (see the broken line in FIG. 1), e.g. during a running up of the pump from zero to the nominal speed of rotation. Accordingly, a plurality of values can also be determined for the viscosity. From this plurality of values for the viscosity then an average viscosity can be determined through an averaging procedure which then represents the final value for the viscosity, which is output after step 15 as the determined viscosity. This procedure increases the precision of the viscosity determination.

This type of viscosity determination is particularly suitable for pumps with a magnetic journalling of the rotor because then the influence of bearing friction, which must be taken into account in mechanical bearings, does not arise. Pumps, in particular blood pumps, with a magnetic journalling of the rotor are for example described in WO-A96/31934.

Figure 2:
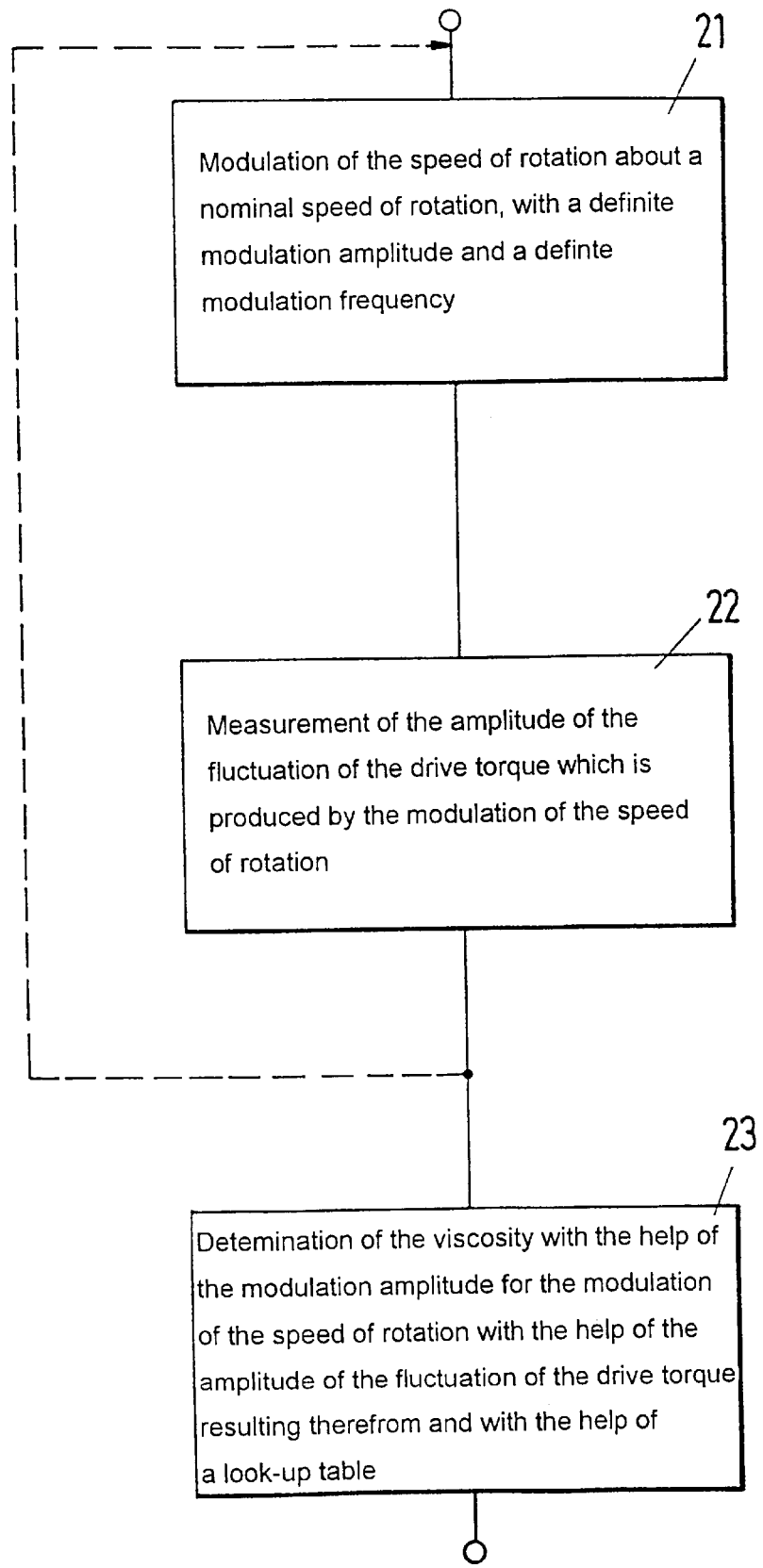
FIG. 2 illustrates a second embodiment variant of the method in accordance with the invention for the determination of the viscosity in the form of a flow diagram (with the outlet of the pump open, hence quasi "on line")

In FIG. 2 a flow diagram of a further variant embodiment of the method in accordance with the invention for the determination of the viscosity is illustrated. This variant embodiment differs substantially from the variant embodiment which is described above with reference to FIG. 1 in so far as in the variant embodiment in accordance with FIG. 2 the outlet of the pump is not closed, but rather the determination of the viscosity takes place with the pump outlet open, that is, quasi "on line". A second series of method variants in which the pump outlet is open could proceed in accordance with this flow diagram.

If one modulates the nominal speed of rotation of the rotor during the pumping with a sufficiently high (angular) modulation frequency and a definite modulation amplitude, then the modulation of the speed of rotation produces no change of pressure or through-flow at the outlet of the pump as a result of the inertia of the liquid; the pump power thus remains practically unchanged.

The speed of rotation can be represented as follows:

$$n(t)=n_0+\Delta n \cdot \sin(\omega_m t) \tag{III}$$

with the variables having the following significance:

n(t) current speed of rotation of the rotor
$n_0$ nominal operating speed of rotation
$\Delta n$ modulation amplitude
$\omega_m$ angular modulation frequency As has already been mentioned the angular modulation frequency is chosen in such a manner that the modulation does not manifest itself in the form of pressure or through-flow fluctuations at the outlet of the pump. Rather, the power supplied through the modulation is completely converted through liquid friction into friction losses. These friction losses are now again dependent on the viscosity of the liquid.

A unique functional relationship between the modulation amplitude (speed of rotation fluctuation), the amplitude of the drive torque fluctuation resulting therefrom and the viscosity can thus be produced. In this the drive torque can be represented as follows:

$$M_A=M_{AO}+\Delta M_A \cdot \sin(\omega_m t) \tag{IV}$$

with $M_A$ current drive torque
$M_{AO}$ average drive torque
$\Delta M_A$ amplitude of the drive torque fluctuation The amplitude $\Delta M_A$ of the drive torque fluctuation is now functionally related to the viscosity $\eta$ and the modulation amplitude $\Delta n$ of the speed of rotation. This can be represented mathematically as follows:

$$\Delta M_A=f(\Delta n, \eta) \tag{V}$$

or, respectively, $$\eta=f(\Delta M_A/\Delta n) \tag{VI}$$

The function of the viscosity described in equation (VI) can again be determined by measurement for each pump and for example be stored in the memory of a microprocessor e.g. in the form of a look-up table. In the described variant embodiment of the method in accordance with the invention a look-up table of this kind has already been determined for the respective pump prior to the operation of the pump and stored in the memory of the microprocessor.

In accordance with FIG. 2 this exemplary embodiment of the method in accordance with the invention for the determination of the viscosity proceeds in such a manner that the speed of rotation of the pump rotor is modulated about a nominal speed of rotation no with a definite modulation amplitude $\Delta n$ and a definite angular modulation frequency $\omega_m$ (see equation (III)) in a first step 21. In this the angular modulation frequency is chosen so high that as a result of the inertia of the liquid the modulation of the speed of rotation results in no change in the pressure or in the through-flow at the outlet of the pump.

A fluctuation of the drive torque about an average drive torque $M_{A0}$ is produced by the modulation of the speed of rotation, and indeed with an amplitude $\Delta M_A$ and the same frequency $\omega^m$ as the angular modulation frequency of the speed of rotation (see relation (IV)). This amplitude can be measured in a step 22, and indeed as the amplitude of the fluctuation of the drive current, which is directly proportional to the drive torque, so that the amplitude of the fluctuation of the drive torque can be easily calculated from the measurement of the amplitude of the fluctuation of the drive current.

In a step 23 the viscosity which results from the values for the modulation amplitude $\Delta n$ of the speed of rotation and the amplitude $\Delta M_A$ of the fluctuation of the drive torque is now determined with the help of the look-up table which is stored in the memory of the microprocessor. If in this the value for the amplitude of the fluctuation of the drive torque and the modulation amplitude for the speed of rotation which are measured in step 22 are not present exactly in the look-up table in the memory of the processor, then the usual interpolation methods are used.

In the described variant embodiments a plurality of measurements of the amplitude of the fluctuation of the drive torque can also be carried out, with in each case different modulation amplitudes of the speed of rotation then being impressed (see the broken line in FIG. 2). Accordingly, a plurality of values for the viscosity can also be determined. From this plurality of average values for the viscosity, an average viscosity can then be determined through averaging procedures, which then represents the final value for the viscosity, which is output after step 23 as the determined viscosity. This procedure increases the precision of the viscosity determination.

The function in relation (IV) is—as one can recognise—dependent on the (angular) modulation frequency $\omega_m$. For a blood pump with a nominal speed of rotation of approximately 5000 rpm and a diameter of the rotor of about 50 mm a particularly good sensitivity (ΔM/Δη) can be achieved at angular modulation frequencies of about 100 rad/s to about 500 rad/s.

Alternatively, the drive torque can also be modulated and the amplitude of the speed of rotation fluctuation resulting therefrom can be measured and these two values then used for the determination of the viscosity. The amplitude of the speed of rotation fluctuation can be measured either directly via a speed of rotation measurement or via the voltage at the rotor, which is approximately directly proportional to the speed of rotation (see above) and can therefore easily be calculated from the voltage at the rotor.

This type of viscosity determination is also suitable especially for pumps with a magnetic journalling of the rotor. Pumps, in particular blood pumps, with a magnetic journalling of the rotor are for example described in WO-A-96/31934.

What is claimed is:

1. A method for the determination of the viscosity of a liquid that is forwarded by a pump, the pump including a rotor for the forwarding of the liquid from an inlet of the pump to an outlet, with the rotor being used for the determination of the viscosity, the method comprising: leaving the rotor in an operating position and determining the viscosity from measurement parameters of one of the pump or of the rotor; controlling the status of the outlet of the pump; generating a trigger signal when the outlet of the pump is closed; activating by the trigger signal, the measurement of at least one measurement parameter of the drive torque of the rotor, the drive current of the rotor and the speed of rotation of the rotor; and determining the viscosity of the liquid from the values of the measurement parameters by using a look-up table wherein the functional relationship of the viscosity and the measurement parameters has already been determined for the respective pump prior to the operation of the pump, wherein the determination of the viscosity of the liquid does not include active excitation of the rotor for the axial deflection from its operating position.

2. A method in accordance with claim 1 wherein the determination of the viscosity includes a plurality of measurements of at least one of the drive torque of the rotor, a drive current of the rotor, and the speed of rotation of the rotor, wherein these plurality of measurements are carried out so that a plurality of values for the viscosity are determined, and wherein from this plurality of values for the viscosity, an average viscosity is determined, which then represents the value for the viscosity.

3. A method in accordance with claim 1 wherein the outlet of the pump is closed prior to the determination of the viscosity based upon the measurement parameters.

4. A method in accordance with claim 3 wherein the measurements of at least one of the drive torque, the drive current, and the speed of rotation of the rotor are effected by the trigger signal, and wherein the trigger signal is conducted further to a control system that initiates the measurements of at least one of the drive torque, a drive current and the speed of rotation of the rotor.

5. A method in accordance with claim 4 wherein the trigger signal is produced by a closure apparatus for the closing of the pump outlet and is conducted to the control system as soon as the outlet of the pump is closed.

6. A method in accordance with claim 4 wherein the trigger signal is produced by a through-flow measurement apparatus that is arranged at the pump outlet and is conducted to the control system as soon as no more through-flow is determined at the outlet of the pump.

7. A method in accordance with claim 4 wherein the trigger signal is produced by a pressure measurement apparatus that is arranged at the outlet of the pump and is conducted to the control system as soon as a pressure is determined at the pump outlet that exceeds a threshold value at a given speed of rotation of the rotor.

8. A method in accordance with claim 4 wherein the pump is a pump with regulation of the speed of rotation, and wherein when an abrupt drop in the drive torque or of the drive current respectively that arises after the closing of the outlet of the pump is detected, the trigger signal is thereupon conducted to the control system.

9. A method in accordance with claim 4 wherein the pump is a pump with drive torque regulation or drive current regulation, respectively, and wherein when an abrupt rise in the speed of rotation that arises after the closing of the pump outlet is detected, the trigger signal is thereupon conducted to the control system.

10. A method in accordance with claim 9 wherein the determination of the viscosity includes a plurality of measurements of at least one of the drive torque of the rotor, a drive current of the rotor, and the speed of rotation of the rotor, wherein these plurality of measurements are carried out so that a plurality of values for the viscosity are determined, and wherein from this plurality of values for the viscosity, an average viscosity is determined, which then represents the value for the viscosity.

* * * * *

UNITED STATES PATENT AND TRADEMARK OFFICE
CERTIFICATE OF CORRECTION

PATENT NO.      : 6,711,943 B1
APPLICATION NO. : 09/333780
DATED           : March 30, 2004
INVENTOR(S)     : Reto Schöb Page 1 of 1

It is certified that error appears in the above-identified patent and that said Letters Patent is hereby corrected as shown below:

Insert the following Claim 11:

11. A method for the determination of viscosity of a liquid that is forwarded by a pump, the pump including a rotor for the forwarding of the liquid from the inlet of the pump to the outlet, with the rotor being used for the determination of viscosity, the method comprising determining the viscosity from measurement parameters of the pump or of the rotor, respectively, while the rotor is left in its operating position; measuring at least one of the drive torque of the rotor, the drive current of the rotor, and the speed of rotation of the rotor as measurement parameters; and determining the viscosity of the liquid by using a functional relationship between the measurement parameters and the viscosity of the liquid; wherein for the determination of the viscosity of the liquid, no active excitation of the rotor for the axial deflection from its operating position takes place.

Signed and Sealed this

Twenty-seventh Day of March, 2007

JON W. DUDAS
*Director of the United States Patent and Trademark Office*